United States Patent [19]

Campbell et al.

[11] Patent Number: 5,827,511

[45] Date of Patent: *Oct. 27, 1998

[54] PRESERVATIVE AND EMBALMING FLUID

[75] Inventors: James W. Campbell; John L. Margrave, both of Houston, Tex.

[73] Assignee: EFH, Inc., Houston, Tex.

[ * ] Notice: The term of this patent shall not extend beyond the expiration date of Pat. No. 5,405,606.

[21] Appl. No.: 805,207

[22] Filed: Feb. 27, 1997

Related U.S. Application Data

[63] Continuation-in-part of Ser. No. 306,645, Sep. 15, 1994, Pat. No. 5,607,668, and a continuation-in-part of Ser. No. 306,696, Sep. 15, 1994, Pat. No. 5,622,695, said Ser. No. 306,645, said Ser. No. 306,696, is a continuation-in-part of Ser. No. 161,893, Dec. 3, 1993, Pat. No. 5,405,606.

[51] Int. Cl.$^6$ ...................................................... A01N 1/00
[52] U.S. Cl. .............................. 424/75; 27/22.1; 27/22.2; 252/407; 514/717
[58] Field of Search ........................... 424/75, 3; 27/22.1, 27/22.2; 252/106, 407; 514/717

[56] References Cited

U.S. PATENT DOCUMENTS

| | | |
|---|---|---|
| 3,057,775 | 10/1962 | Rendon . |
| 3,197,366 | 7/1965 | Cannon et al. . |
| 3,249,502 | 5/1966 | Hayden . |
| 3,264,182 | 8/1966 | Langner . |
| 3,293,127 | 12/1966 | Beck . |
| 3,573,082 | 3/1971 | Fremling . |
| 3,852,418 | 12/1974 | Tucker, Jr. . |
| 3,912,809 | 10/1975 | Rendon . |
| 4,021,537 | 5/1977 | Saurino . |
| 4,121,944 | 10/1978 | VanLandingham . |
| 4,263,278 | 4/1981 | Saurino et al. . |
| 4,339,462 | 7/1982 | Muntwyler . |
| 4,404,181 | 9/1983 | Mauthner . |
| 4,946,669 | 8/1990 | Siegfried et al. . |
| 5,196,182 | 3/1993 | Ryan . |
| 5,260,048 | 11/1993 | Ryan . |
| 5,374,378 | 12/1994 | Lorentzen et al. . |
| 5,384,125 | 1/1995 | Dipippo et al. . |
| 5,405,606 | 4/1995 | Campbell et al. . |
| 5,496,858 | 3/1996 | Eggensperger . |
| 5,607,668 | 3/1997 | Campbell et al. . |
| 5,622,695 | 4/1997 | Campbell et al. . |

FOREIGN PATENT DOCUMENTS

| | | |
|---|---|---|
| 0264658 | 4/1992 | European Pat. Off. . |
| PCT/US94/ 13822 | 3/1995 | WIPO . |

OTHER PUBLICATIONS

Harold T. McKone, "Embalming: A Rite Involving Early Chemistry", Todays Chemist at Work, Apr., 1994 pp. 69–70.
Lawrence E. Wineski and Arthur E. English, "Phenoxyethanol as a Nontoxic Preservative in the Dissection Laboratory", Acta Anta 1989:136: 155–158.
James H. Bedino "Millenium/New Era –Champion's Third Generation of Embalming Chemicals", Champion Report, (no date).
Third Generation of Embalming Chemicals, Champion Report (no date).
Carolina Carosafe, "Preserved Animals", (no date).
Connecticut Valley, "Preserved Material", (no date).
Nebraska Scientific, "Quality Specimens", (no date).
Streck Tissue Fixative, Streck Laboratories, Inc., Oct., 1992.
Ward's "Preserved Materials", (no date).
Champion, Millenium New Era Christine Ultra Brochure and Material Safety Data Sheet, dated Oct. 1993.
Schwartz, Dr. Arthur and Barbara Schwartz, *Pollution Prevention Through Use of a Formaldehyde–Free Biological Preservative*, Apr. 1994, Belle Mead, NJ.
James H. Bedino, "Expanding Encyclopedia of Mortuary Practices"No. 613, 1992, pp. 2466–2469.
Champion "Millenium New Era Cavity 48 and Material Safety Data Sheet", dated Oct. 1993.

*Primary Examiner*—Robert H. Harrison
*Attorney, Agent, or Firm*—Fish & Richardson P.C.

[57] ABSTRACT

An improved preservative and embalming fluid and method has been developed. The embalming fluid is a mixture including glutaraldehyde, an aromatic ether of ethanol, e.g. phenoxyethanol, at least one alcohol, and a polyhydric alcohol humectant. The formulation has no formaldehyde. The concentrate is diluted with water for use and may include a borate buffer.

18 Claims, No Drawings

PRESERVATIVE AND EMBALMING FLUID

RELATED APPLICATIONS

This application is a continuation-in-part of Ser. Nos. 08/306,645 filed Sep. 15, 1994 entitled "Embalming Composition and Method" by James W. Campbell and John L. Margrave, now U.S. Pat. No. 5,607,668, and 08/306,696 filed Sep. 15, 1994 entitled "Anatomical and Biological Preservative and Method" by James W. Campbell and John L. Margrave, now U.S. Pat. No. 5,622,695, which are both continuation-in-parts of Ser. No. 08/161,893 filed Dec. 3, 1993 entitled "Embalming Composition and Method" now U.S. Pat. No. 5,405,606 issued Apr. 11, 1995 by James W. Campbell and John L. Margrave which related applications are wholly incorporated by reference herein.

BACKGROUND OF THE INVENTION

Anatomical and biological preservatives and embalming fluids typically used contain significant quantities of formaldehyde. The formaldehyde solutions used for preservation fix the tissues of the specimen and preserve the specimen from decay. Many plant and animal species are preserved for academic study. Smaller life forms are immersed in a preservative. Larger vascular animals are injected in the circulatory system and elsewhere with a preservative. Although formaldehyde solutions have historically been the preservative fluid of choice, there are a number of drawbacks. Formaldehyde is associated with certain health and environmental risks. Also, formaldehyde can cause problems with preserving the specimen, because it dehydrates the tissue.

Alternative preservation fluids have been proposed including phenols, alcohols, and certain acid preparations. Other methods have included initially fixing the specimen in formaldehyde, rinsing the specimen and placing the specimen in another solution that does not include formaldehyde.

Human remains are used for morbid anatomy study are included in the specimens needing preservation. The desire to eliminate exposure to formaldehyde has been examined by investigators involved in cadaver preservation. Wineski et al., "Phenoxyethanol as a Nontoxic Preservative in the Dissection Laboratory," *Acta Anat.* Vol. 136 pp. 155–158 (1989). The cadavers were embalmed by injection with about 24 liters of formaldehyde fluids. After embalming the cadavers were immersed or completely wrapped with cloth heavily soaked in phenoxyethanol. Exposure of workers to phenoxyethanol is preferable environmentally to formaldehyde. However, the success of the technique depended on good initial preparation of the cadavers with a formaldehyde fluid.

Other alternatives to formaldehyde include a formulation made with a 1,4-dioxane ring compound, U.S. Pat. No. 3,264,182; a process of pre-fixation with formaldehyde followed by preservation in glycols, U.S. Pat. No. 3,573,082; and solutions of starch glycerite for marine animals to preserve color, U.S. Pat. No. 4,121,944.

The formaldehyde embalming solutions are injected into the arteries and also introduced into the body cavity. Generally, the cavity formulation is more concentrated because the naturally occurring fluids in the body cavity will dilute the formaldehyde formulation. The formaldehyde solutions also typically contain other additives such as humectants. Although formaldehyde solutions have historically been the embalming fluids of choice, there are a number of drawbacks as discussed above for biological preservatives. Formaldehyde can cause problems with the presentation of the body, because it dehydrates the tissue.

In U.S. Pat. No. 3,057,775 issued Oct. 9, 1962 to Rendon entitled "Embalming Composition", glutaraldehyde was used instead of formaldehyde as a preservative in the embalming fluid. Glutaraldehyde was mixed with other preservatives in the formulations disclosed. If glutaraldehyde were used as the sole preservative, it would not be less than 7% of the solution. However, glutaraldehyde should be stabilized in the fluid to prevent oxidation and may polymerize in certain concentrations. Glutaraldehyde is tolerable to handle and does not have a noxious odor. Also, glutaraldehyde does not dehydrate tissue.

U.S. Pat. No. 3,912,809 issued on Oct. 14, 1975 to Rendon entitled "Disinfecting Embalming Composition", discloses a fluid that is 2% by weight glutaraldehyde and an alkalizing agent to adjust the pH of the solution to pH 8~8.5. The glutaraldehyde is not stable in the alkalizing solution for more than a few weeks and the disclosure recognizes the problem of polymerization when glutaraldehyde is present in large concentrations. According to the patent, the shelf life problem is resolved by initially preparing two solutions. One is the glutaraldehyde solution which typically also includes formaldehyde and the other is the alkalizing solution. The two solutions are mixed as needed. This composition is reported to reduce significantly the microbial growth in human remains.

A need exists for a preservative and embalming fluid that is safe to handle and is relatively simple to prepare for use. Previous alternatives to formaldehyde fluids have been solutions with stability problems associated with higher levels of glutaraldehyde, were cumbersome to use or were extremely corrosive.

SUMMARY OF THE INVENTION

An improved preservative and embalming fluid has been developed. The fluid is suitable for use for specimens that are immersed or injected with the fluid into the vascular system. The fluid is a concentrated mixture of glutaraldehyde, at least one aromatic ether of ethanol such as phenoxyethanol, at least one alcohol, and a humectant. The humectant can be a polyhydric alcohol such as glycerol, hexylene glycol or propanediol.

The composition may be prepared initially as a concentrate with or without water, then diluted with water to the desired strength. The fluid may contain various additives conventionally used in preservatives, including a color additive, pH buffer, an antioxidant, odorant and mixtures thereof. A borate buffer is included in the buffers used in the fluid. The fluid exhibits excellent cidal activity for microbes such as viruses. A biocide may also be added for additional cidal activity in addition to the fluid components to kill mold and other microbes when the specimen is going to be used for a prolonged time.

DETAILED DESCRIPTION OF THE INVENTION

The improved preservative and embalming fluid of the present invention is a unique mixture of glutaraldehyde, at least one aromatic ether of ethanol, at least one humectant, and at least one alcohol. Generally, the fluid is diluted with water prior to use. The fluid can be prepared in dilutions appropriate for whole specimen preservative and vascular injection for biological studies. The fluid can be used for embalming including arterial injection and cavity fluid.

The concentrate formulation includes the following components by volume: glutaraldehyde from about 1.0% to about 8.0%, aromatic ether of ethanol such as phenoxyethanol from about 1.4% to about 6.0%, humectant from about 1.4% to about 9%, and an alcohol from about 50% to about 74%; water is added to make up the volume if necessary. A humectant used in the fluid can be a polyhydric alcohol or mixtures of more than one polyhydric alcohol. Particular polyhydric alcohols are glycerol and 1,2 propanediol. Another polyhydric alcohol humectant is hexylene glycol. An aromatic ether of ethanol used in the fluid is phenoxyethanol. Ethoxyethanol may be added to the fluid in the range of about 0.6% to about 4.0% The recited components are not intended to limit the scope of the inventions and alternative components within the scope of the invention will be recognized by those skilled in the art.

The following Example 1 is an illustration of the concentrate fluid.

EXAMPLE 1

| Components | Percent by Volume |
| --- | --- |
| Ethanol | 62.14% |
| Gycerol | 2.59% |
| Glutaraldehyde | 4.00% |
| Propylene Glycol | 1.28% |
| Phenoxyethanol | 4.79% |
| Ethoxyethanol | 1.55% |
| Buffer | <0.2% |
| Water | 19.65% |
| Dye | <0.07% |

Dimethyl sulfoxide or another compound that acts as a penetrant such as EDTA may also be used typically in the range of about 0.5% to about 1.0%.

Ethanol is used as an alcohol in the formulation. However, amounts of isopropanol, methanol or mixtures thereof can be used as a denaturant or otherwise in the formulation. The following Example 2 is a concentrate with isopropyl alcohol included.

EXAMPLE 2

| Components | Percent by Volume |
| --- | --- |
| Ethanol | 60.0% |
| Isopropanol | 3.1% |
| Glycerol | 2.6% |
| Glutaraldehyde | 4.0% |
| Phenoxyethanol | 4.4% |
| Ethoxyethanol | 1.6% |
| Propylene Glycol | 1.3% |
| Boric Acid Buffer | 2.6% |
| Water | 18.0% |

The pH of the concentrate is adjusted to about pH 7.8 to about pH 8.5. The buffer used in Example 2 is a boric acid buffer adjusted with sodium hydroxide. The buffer concentration in the concentrate is about 0.1236% $H_3BO_3$ and about 0.14% NaOH. The pH is about 8.0 at 20.6° C. The buffering system in Example 2 is made up with water prior to addition to the concentrate to about 0.38M $H_3BO_3$ and 0.066M NaOH so the buffer percentage also represents water from the buffer system. Other buffer systems such as sodium phosphate may be used.

The concentrate may be used in dilutions from about 1:1 to more dilute depending on the application. Dilutions as low as 1:5 have been found satisfactory for embalming purposes.

In addition to the components in Examples 1 and 2, an antioxidant may be included to maintain the stability of the glutaraldehyde. A biocide may be added to further deter microbial growth. For example, a bactericide or a viricide may be included such as benzalkonium chloride or other quaternary ammonium compounds. In addition, other additives conventionally used in preservation fluids such as color additives may be included. Color additives are used in vascular systems of biological specimens for identification. It is not intended to limit the claimed formulation to exclude additives known to be used in preservation compositions that would be compatible with the formulation of the present invention.

The improved composition includes glutaraldehyde in relatively small concentrations. Anatomical tissues treated with this fluid have exhibited good color retention in muscle tissue of cadavers. The specimens have no odor and are easy to work with. The more glutaraldehyde is used in the formulation the more rigid the joints will be of specimens with a skeletal structure.

The dilution factor can be adjusted depending on the application. A fluid for cavity preservation is more concentrated while the arterial fluid is less concentrated.

Typically, the fluid is injected by arterial delivery into the subject and allowed to penetrate the tissue. The fluid and method of this invention exhibits excellent penetration and delivery characteristics as compared to formaldehyde based fluids. Also, discolorations caused by hematomas and other conditions were lessened when the deceased was embalmed using the improved fluid of the present invention. The improved fluid also relieves blood clots which can impair the preservation of the body. This is particularly important if the embalming process is delayed after death and blood clots form prior to injection of the fluid. The fluid of the present invention appears to break up the blood clots and improve delivery of the fluid through the arteries. The formaldehyde fluids do not exhibit alleviation of discoloration or break up blood clots as compared to the fluid and method of the improved embalming composition described herein.

Generally, the arterial fluid is made up of a less concentrated solution within the prescribed ranges. The cavity fluid is introduced into the central body cavity of the deceased, and this fluid is generally more concentrated within the ranges. The glutaraldehyde component in the present fluid when diluted is a relatively small concentration at levels not susceptible to polymerization. Also, the improved fluid is stable and does not require multiple mixing steps with more than one solution. The same solution may be diluted as desired for use as an arterial or cavity fluid.

The examples and methods described herein are not intended to limit the scope of the invention. Those skilled in the art will recognize variations and substitutions in the composition and method that fall within the scope of the invention.

We claim:

1. A preservative and embalming fluid concentrate comprising glutaraldehyde in the range of about 1.0% to about 8.0% by volume of the concentrate;

an alcohol in the range of about 50% to about 74% of the concentrate;

phenoxyethanol in the range of about 1.4% to about 6.0% of the concentrate; and at least one polyhydric alcohol in the range of about 1.4 to about 9% of the concentrate.

2. A preservative and embalming fluid concentrate of claim 1 additionally comprising ethoxyethanol in the range of about 0.6% to about 4.0%.

3. A preservative and embalming fluid concentrate of claim 1 additionally comprising a pH buffer.

4. A preservative and embalming fluid concentrate of claim 3 wherein said buffer comprises a borate buffer.

5. A preservative and embalming fluid concentrate of claim 1 wherein said alcohol is ethanol.

6. A preservative and embalming fluid concentrate of claim 5 additionally comprising as the alcohol one of the group consisting of isopropanol, methanol and mixtures thereof.

7. A preservative and embalming fluid concentrate of claim 1 wherein the polyhydric alcohol is selected from the group consisting of glycerol, 1–2 propanediol, hexylene glycol and mixtures thereof.

8. A preservative and embalming fluid concentrate of claim 1 additionally comprising a color additive.

9. A preservative and embalming fluid concentrate of claim 1 additionally comprising an antioxidant.

10. A preservative and embalming fluid concentrate of claim 1 additionally comprising a biocide.

11. A preservative and embalming fluid concentrate of claim 1 additionally comprising water.

12. A preservative and embalming fluid concentrate of claim 2 additionally comprising water.

13. A preservative and embalming fluid concentrate of claim 3 additionally comprising water.

14. A preservative and embalming fluid concentrate of claim 1 wherein the fluid concentrate is diluted for use with water up to 1 part fluid concentrate to 5 parts water.

15. A preservative and embalming fluid concentrate of claim 3 wherein the fluid concentrate is adjusted to about pH 7.8–8.5 by the pH buffer.

16. A preservative and embalming fluid concentrate of claim 4 wherein the fluid concentrate is adjusted to about pH 7.8–8.5 by the pH buffer.

17. A preservative and embalming fluid concentrate diluted as in claim 14 additionally comprising a pH buffer in the diluted concentrate to adjust the pH to about 7.8–8.5.

18. A preservative and embalming fluid concentrate of claim 17 wherein the pH buffer is a borate buffer.

* * * * *